United States Patent [19]

Cloke

[11] Patent Number: 4,973,498

[45] Date of Patent: Nov. 27, 1990

[54] VOLATILE LANTHANUM COMPLEXES FOR USE IN CHEMICAL VAPOR DEPOSITION

[75] Inventor: Frederick G. N. Cloke, Brighton, England

[73] Assignee: The British Petroleum Company p.l.c., London, England

[21] Appl. No.: 420,906

[22] Filed: Oct. 13, 1989

Related U.S. Application Data

[62] Division of Ser. No. 206,208, Jun. 13, 1989, Pat. No. 4,894,446.

[30] Foreign Application Priority Data

Jun. 16, 1987 [GB] United Kingdom ................. 8714072

[51] Int. Cl.$^5$ .............................................. C23C 16/18
[52] U.S. Cl. ..................................... 427/250; 427/252

[58] Field of Search ............... 427/123, 124, 250, 252; 423/21.1; 556/1

[56] References Cited

U.S. PATENT DOCUMENTS 4,882,206 11/1989 Erbil .................................... 427/252

Primary Examiner—Shrive Beck
Assistant Examiner—Margaret Bueker
Attorney, Agent, or Firm—Brooks Haidt Haffner & Delahunty

[57] ABSTRACT

Homoleptic bis ($\pi$-arene) yttrium or lanthanide complexes of formula $ML_2$, wherein M is yttrium or a lanthanide metal and the L ligands are di or trisubstituted benzene derivatives, are provided. Certain of the complexes are volatile and are therefore of interest in the chemical vapor deposition. A process for their manufacture is described.

8 Claims, No Drawings

VOLATILE LANTHANUM COMPLEXES FOR USE IN CHEMICAL VAPOR DEPOSITION

This is a division of parent application Ser. No. 07/206,208 filed Jun. 13, 1989 now U.S. Pat. No. 4,894,446.

The present invention relates to new homoleptic bis (π-arene) yttrium or lanthanide complexes.

There are few known π-arene complexes of the f-block elements and only one such complex [Sm (π-C$_6$(CH$_3$)$_6$)(AlCl$_4$)$_3$] contains a lanthanide ion (see for example Inorg. Chim. Acta., 1971, 5, 439; Organometallics, 1985, 4, 942 and 1986, 5, 637 and J.A.C.S., 1986, 108, 4657). In all of these complexes the metal ion is highly charged (M$^{3+}$ or M$^{4+}$) and the bonding can be viewed as an electrostatic attraction between the positively charged metal ion and the π-electron density of the arene ring. To date however, no zero oxidation state bis (π-arene) lanthanide complexes have been reported.

It has also been disclosed that, whilst bis (π-arene) complexes of zirconium and hafnium with benzene, toluene or mesitylene are too unstable to be isolated, complexes with the bulky 1,3,5-tri(tertbutyl)benzene) can be made (see J. Chem, Soc. 1667, 1986).

According to the present invention there is provided homoleptic bis (π-arene) lanthanide complexes having the general formula ML$_2$ where M is yttrium or a lanthanide and the L ligands are independently selected from

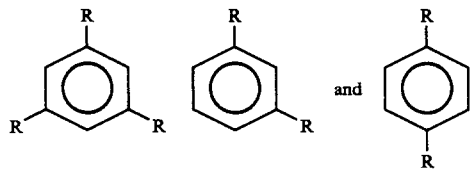

wherein the R groups are independently selected from (a) C$_3$ to C$_{20}$ hydrocarbyl radicals or (b) Si(R$^1$)$_3$ or CH(Si(R$^1$)$_3$)$_2$ groups wherein the R$^1$ groups are independently C$_1$ to C$_{20}$ hydrocarbyl radicals.

The L ligands defined above are suitably di or tri substituted benzenes since it is believed that monosubstituted are toothermally unstable to be isolated. Likewise, bis (π-arene) complexes with ligands such as meta-xylene, para-xylene and mesitylene are unisolable. Hence it is believed that each R group in the ligand L must have at least three carbon atoms.

For a given number of carbon atoms in R, it is preferable that R offers as much 'steric hinderance' as possible, i.e. ability to interact with other similar groups. Thus, in general, for a given carbon number, those R groups having tertiary carbon atoms, will be preferred over those having secondary carbon atoms which will in turn be preferable over those having only primary. Typical examples of suitable R groups are those having the formula C(R$^2$)$_3$ wherein the R$^2$ groups are independently C$_1$ to C$_6$ alkyl, most preferably methyl, ethyl or propyl.

The R groups may alternatively be selected from tertiary silyl groups having the formula Si(R$^1$)$_3$ or CH(Si(R$^1$)$_3$)$_2$ wherein the R$^1$ groups are independently selected from C$_1$ to C$_{20}$ hydrocarbyl radicals. Preferred examples are the trimethylsilyl, and triethylsilyl groups.

The remaining positions on the benzene ring may be taken by hydrogen atoms or non-bulky substituents such as methyl or ethyl groups.

The bis (π-arene) complexes of the present invention may suitable be prepared by the technique of metal vapour synthesis. This technique involves cocondensing a stream of the vapourised lanthanide atoms with a stream of the vapourised ligand L at very low temperature. It has been described in, for example, J. Chem. Soc., (Dalton), 1981, 1938.

According, therefore, to an embodiment of the present invention there is provided a process for preparing homoleptic bis (π-arene) yttrium or lanthanide complexes on the type defined above comprising the steps of:

(a) vapourising yttrium or a lanthanide metal to produce a vapour of yttrium or lanthanide metal atoms,
(b) cocondensing the vapour of yttrium or the lanthanide metal atoms with vapourised ligand L at a temperature below −100° C.,
(c) thereafter warming the cocondensate to a temperature above −100° C.

After step (c) above the homoleptic bis (π-arene) yttrium or lanthanide metal complex can be recovered using known techniques including extraction, filtration and concentration under reduced pressure. The preparation and subsequent manipulation of the homoleptic bis (π-arene) yttrium or lanthanide metal complexes should be carried out under an inert atmosphere in the absence of moisture.

It has been found that the Yttrium, Neodymium, Gadolinium, Terbium, Dysprosium, Holmium, Erbium and Lutetium complexes with 1,3,5-tri(tertbutyl)benzene are stable at room temperature but decompose at temperatures above 100° C. Furthermore such complexes are volatile. Such properties mean that the complexes are useful in the chemical vapour deposition of metals.

According to a further embodiment of the present invention there is provided a process for depositing a layer or film of yttrium or lanthanide metal upon a substrate which comprises contacting the vapour of a homoleptic bis (π-arene) lanthanide complex with the substrate at a temperature in excess of 100° C.

Deposition is preferably effected at a temperature between 110° and 150° C.

The present invention is now illustrated by the following Examples.

EXAMPLE 1

(a) General

All manipulations were carried out under argon or in vacuo with rigorous exclusion of air and moisture using standard inert atmosphere techniques. Solvents were dried by standard procedures.

The metal vapour synthesis were carried out using an apparatus of the type described in J. Chem. Soc., (Dalton), 1981, 1938 having a positive hearth. A small ingot of the lanthanide metal was irradiated with a beam of high voltage electrons emanating from a filament. The current in the filament was continuously varied to ensure a constant emission current.

(b) Synthesis of bis (1,3,5-tri(tertbutyl)benzene) Yttrium

Vapourised yttrium [ca 0.9 g (10 mmol)] was cocondensed with 25 g (100 mmol) of 1,3,5-tri(tertbutyl) benzene at −196° C. over a period of 2 hours. The cocondensate was allowed to warm to room temperature under argon and the solid products extracted from the apparatus with n-hexane (ca 750 cm$^3$). The resultant deep purple solution was filtered through a bed of Celite on a frit and the solvent removed under reduced pressure. Excess of the 1,3,5-tri(tertbutyl)benzene was then removed by the sublimation at 60° C./10$^{-4}$ mbar and the residue extracted with n-pentane (ca 150 cm$^3$). The resulting solution was again filtered through Celite. Concentration of the resultant solution under reduced pressure and cooling to −30° C. afforded deep purple crystals of the complex. The crystals were collected, washed with n-pentane at −80° C. (2×10 cm$^3$) and dried in vacuo. Yield ca 2.4 g (40% based on yttrium).

(c) Analysis

ESR (in frozen methylcyclohexane at −196° C.): $g_{11}=2.085$ doublet. A=3.0 m T. $g_1=2.005$.

Microanalytical data: C 74.41 (74.32 theoretical). H 10.58 (10.40 theoretical).

EXAMPLE 2

Synthesis of bis (1,3,5-tri(tertbutyl)benzene) gadolinium

The procedure of Example 1 was followed except that vapourised gadolinium (ca 0.7 g, ca 5 mmol) was used in place of yttrium. The gadolinium complex was isolated as deep purple crystals. Yield ca 1.5 g (40% based on gadolinium). Microanalytical data C 66.59 (66.51); H 9.45 (9.30).

EXAMPLE 3

Example 1 was repeated except that 0.4 g (2.8 mmol) of vapourised neodymium was used. 0.5 g (25% yield) of the neodymium complex was obtained (blue crystals). Microanalysis C 67.92 (67.87); H 9.63 (9.49).

EXAMPLE 4

Example 1 was repeated except that 0.9 g (5.66 mmol) of terbium was used. 1.7 g (40% yield) of the terbium complex was obtained (purple crystals).

EXAMPLE 5

Example 1 was repeated except that 2.0 g (12.3 mmol) of dysprosium was used. 2.0 g (30% yield) of the dysprosium complex was obtained (purple crystals).

EXAMPLE 6

Example 1 was repeated except that 0.87 g (5.2 mmol) of holmium was used. 1.5 g (40% yield) of the holmium complex was obtained (deep pink crystals). Microanalysis C 65.25 (65.73) H 9.17 (9.19).

EXAMPLE 7

Example 1 was repeated except that 1.3 g (7.7 mmol) of erbium was used. 1.7 g (40% yield) of the erbium complex was obtained (red crystals).

EXAMPLE 8

Example 1 was repeated except that 0.87 g (4.97 mmol) of lutetium complex was used. 1.3 g (40% yield) of the lutetium complex was obtained (red-green crystals).

EXAMPLE 9

A stream of vapour of the yttrium complex prepared in Example 1 is passed from a reservoir (e.g. a glass flask) through a glass tube heated to 130° C. Flow of vapour can be achieved, for example, by drawing the vapour through the glass tube under the action of a vacuum pump. A black deposit on the inside of the glass tube is indicative of the deposition of yttrium metal and minor amounts of impurities.

EXAMPLES 10–16

Example 9 is repeated with each of the complexes prepared in Examples 2 to 8. A black deposit on the inside of the glass tube is obtained in each case indicative of the particular metal and its impurities.

I claim:

1. A process for depositing a layer or film of yttrium or a lanthanide metal upon a substrate which comprises contacting the vapor of a homoleptic bis ($\pi$-arene) complex having the general formula ML$_2$ wherein M is yttrium or a lanthanide metal and the L ligands are independently selected from the group consisting of

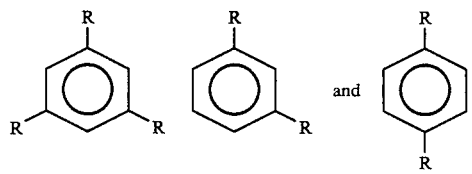

wherein the R groups are independently selected from (a) C$_3$ to C$_{20}$ hydrocarbyl radicals or (b) Si(R$^1$)$_3$ or CH(Si(R$^1$)$_3$)$_2$ groups wherein R$^1$ groups are independently C$_1$ to C$_{20}$ hydrocarbyl radicals with a heated substrate.

2. A process as defined in claim 1 wherein the R groups have the formula C(R$^2$)$_3$ wherein R$^2$ group are independently C$_1$ to C$_6$ alkyls.

3. A process as defined in claim 1 wherein the R groups possess either a tertiary or secondary carbon atom.

4. A process as defined in claim 2 wherein both R groups are 1,3,5-tri(tertbutyl)-benzene.

5. A process as defined in claim 4 wherein M is either yttrium or gadolinium.

6. A process as defined in claim 4 wherein M is selected from the group consisting of neodymium, terbium, dysprosium, drolinium, erbium and lutetium.

7. A process as defined in claim 1 wherein at least one R$^1$ group is either trimethylsilyl or triethylsilyl.

8. A process as defined in claim 1 wherein the deposition temperature is in the range of 100° to 150° C.

* * * * *